United States Patent
Shafi et al.

(10) Patent No.: US 12,202,780 B1
(45) Date of Patent: Jan. 21, 2025

(54) PROCESS FOR DEBROMINATION OF NOVEL BROMINATED FLAME RETARDANTS USING Zn-BASED ADDITIVES

(71) Applicant: United Arab Emirates University, Al Ain (AE)

(72) Inventors: Mohamed Shafi, Al Ain (AE); Labeeb Ali, Al Ain (AE); Mohammednoor Al Tarawneh, Al Ain (AE); Abdul Razack Hajamohideen, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 18/794,655

(22) Filed: Aug. 5, 2024

(51) Int. Cl.
| | |
|---|---|
| *C07C 1/32* | (2006.01) |
| *A62D 3/34* | (2007.01) |
| *A62D 3/40* | (2007.01) |
| *B01J 20/06* | (2006.01) |
| *C07C 37/00* | (2006.01) |
| *A62D 101/22* | (2007.01) |

(52) U.S. Cl.
CPC ............. *C07C 1/321* (2013.01); *A62D 3/34* (2013.01); *A62D 3/40* (2013.01); *B01J 20/06* (2013.01); *C07C 37/005* (2013.01); *A62D 2101/22* (2013.01)

(58) Field of Classification Search
CPC ......... C07C 1/321; C07C 37/005; A62D 3/34; A62D 3/40; B01J 20/06
See application file for complete search history.

(56) References Cited

PUBLICATIONS

Kuttiyathil et al. Debromination of novel brominated flame retardants using Zn-based additives: A variable thermochemical approach in the mitigation of toxic effects during e-waste recycling. Environmental Pollution, vol. 346, 123645. (Year: 2024).*

* cited by examiner

*Primary Examiner* — Sikarl A Witherspoon
(74) *Attorney, Agent, or Firm* — MH2 Technology Law Group, LLP (57) ABSTRACT

There is disclosed a process for debromination of novel brominated flame retardants (NBFRs) through co-pyrolysis with zinc oxide (ZnO) and franklinite ($ZnFe_2O_4$) to effectively restrict brominated species emission from NBFRs during thermal degradation. The method addresses environmental concerns by converting tetrabromobisphenol A 2,3-dibromopropyl ether (TBBPA-DBPE) and tetrabromobisphenol A diallyl ether (TBBPA-DAE) into bromine-free hydrocarbons. Utilizing Zn-based metal oxides from electrical arc furnace dust (EAFD), this process transforms them into metal bromides, facilitating selective zinc extraction. Thermogravimetric analysis guides pyrolysis at up to 500° C., revealing ZnO's efficacy in capturing ~92% of HBr gas and producing minimal brominated compounds (relative area, 0.83%). Phenol emerges as a significant condensable product, while inorganic gases and methane dominates the non-condensable fraction. The retained metal bromides in pyrochar and <8% HBr gas emissions underscore ZnO's debromination potential. This method also suggests ZnO's application for dehalogenating other polymers and using spinel ferrites in combating brominated polymers.

20 Claims, 5 Drawing Sheets

PROCESS FOR DEBROMINATION OF NOVEL BROMINATED FLAME RETARDANTS USING Zn-BASED ADDITIVES

FIELD OF THE INVENTION

The present invention relates to the field of thermal recycling of novel brominated flame retardants (NBFRs), and more particularly to process for efficiently debrominating the NBFRs using zinc-based additives.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

The issue of e-waste management has become increasingly pressing, with only 17.4% of e-waste being recycled globally. In 2019, the value of all the e-waste produced was estimated at over US$57 billion. By 2030, global e-waste generation is expected to reach a whopping amount of 75 million tons. Among the various fire retardants available in the market, the brominated flame retardants (BFRs) are the most widely preferred fire retardant in the electrical and electronics industry due to its superior fire retarding properties. They impede the combustion cycle of fire by releasing bromine to react with OH free radicals during a fire breakout. While BFRs are critical for safety during the life cycle of any electrical or electronic instrument, they pose significant environmental threats once these devices are discarded. The toxic effects of legacy BFRs are well-documented, necessitating strict mitigation measures.

However, the emergence of novel BFRs (NBFRs) as an alternative to legacy BFRs presents new challenges. Currently there aren't many studies on the novel BFRs and their recycling techniques as it has been perceived lately as an emerging contaminant. Though the novel BFRs pose the same threat as that of legacy BFRs, no legal restrictions or embargo has been sanctioned on these novel BFRs as they have not been categorized as persistent organic pollutant (POPs) till date. Recent studies have reported the occurrence of novel BFRs in indoor dust, various waterbodies and thereby in aquatic animals in the vicinities of the electrical and electronic industries. These contaminants have been linked to toxic effects on the human endocrine system and neurobehavioral health, as reported in recent studies. Therefore, there is an urgent need to develop environmentally friendly and practical debromination approaches to prevent bromine release from NBFR-laden objects.

Technological revolution, upgradation in consumer products and the never-ending insisting consumer behaviour of the current generation have led to frequent replacement, upgrades and comparatively shorter life cycles of electronic and electrical goods. Such puerile practices have exacerbated the accumulation of waste of electrical and electronic equipment (WEEE) in an unprecedented manner. By 2030, global e-waste generation is expected to reach a whopping amount of 75 million tons as the average WEEE production has already crossed 54 million tons in 2019. With inadequate recycling of the e-waste globally, the value of all the e-waste produced in 2019 was estimated to be over US$57 billion. Informal handling of e-waste raises questions on ecological ethics, social justice and incongruous land use and often leads to contamination of soil, air, and water, with adverse effects on human health. A former vegetative wetland Agbogbloshie, Accra in Ghana now houses one of the biggest global landfills for e-waste. The European Union has passed legislation and directives to encourage the reuse, recovery, and recycling of e-waste. Several Asian and South American countries strive hard to achieve the Sustainable Development Goals invigorated by the UN in 2020.

Brominated fire retardants (BFR) are the most sought-after fire retardants especially prevaleny in electrical and electronic industries. Illegitimate storage and handling of e-waste have led to the occurrence of BFRs and contamination of the soil, air and even the aquifers beneath due to infiltration; causing serious issues to the human endocrine system. Open incineration of the e-waste as a disposal method, leads to even more severe health problems due to the release of polyhalogenated dibenzo dioxins/furans and hydrogen bromide (HBr) gases into the atmosphere. The Stockholm Convention of the United Nations Environment Program and various other legislative actions worldwide have phased out legacy BFRs, paving the way for the production and utilization of the so-called novel BFRs, NBFRs. The NBFRs could be recognized as either newly introduced fire retardants in the market or observed in the environment by the degradation of legacy BFRs as reported by many studies. All these anthropogenic BFRs are pervasive and considered persistent organic pollutants as they have a bio-magnification factor of >5000, an environmental half-life of >2 months and an atmospheric half-life exceeding 2 days. The occurrence of NBFRs in indoor dust, various waterbodies and thereby in aquatic animals has been reported in recent studies. The toxic effects of NBFRs on the human endocrine system were investigated and the consequences on neurobehavioral effects were discussed by many research studies. The probability of occurrence of NBFRs, (especially two typical NBFRs, namely, Tetrabromobisphenol A 2,3-dibromopropyl ether (TD) and Tetrabromobisphenol A diallyl ether (TAE)) in various environmental matrices, associated bromine release from NBFR-laden objects and their toxicological impacts is well-documented and necessitates the development of effective debromination technologies.

Though NBFRs have replaced legacy BFRs, current literature studies and analysis of prior art materials highlight an explicit knowledge gap in the handling and disposal of NBFRs. No studies have extensively explored the pyrolytic or oxidative catalytic treatment of these compounds. Given their derivation from widely used legacy BFRs, it is crucial to understand the chemical reactions involved in their decomposition during the widely applied pyrolytic catalytic upgrading operations.

Previous research has demonstrated the use of different metallic oxides as halogen scavengers during the pyrolysis of legacy BFRs. Notably, electric arc furnace dust (EAFD), containing high quantities of franklinite and zincite, is an industrial waste facing disposal challenges as is generated in huge quantities. Franklinite has been reported by previous works to show promising dehalogenation efficiency, reducing the onset temperature of dehydrochlorination in PVC by 37° C. However, the halogen-scavenging properties of metal oxides is not leveraged so far due to its limitation that it has been primarily used with legacy BFRs, and there is a lack of comprehensive studies specifically addressing the effectiveness of this approach for NBFRs. Additionally, the scalability and environmental impact of using these metallic oxides in large-scale applications remain underexplored.

Based on the above explained, there exists a need for an improved system for the efficient chemical recycling of NBFRs, utilizing an improved chemical process that ensures effective debromination, scalability, and minimal environmental impact, thus overcoming the drawbacks of the traditionally employed systems.

SUMMARY OF THE INVENTION

Therefore it is an object of the present invention to propose a process or method for efficiently debrominating novel-brominated flame retardants (NBFRs) using zinc-based metal oxides as a viable thermochemical recycling approach, aimed at preventing the release of bromine into the atmosphere and to generate a bromine-free stream of hydrocarbons.

There is disclosed a process for debromination of novel-brominated flame retardants (NBFRs) using Zn-based metal oxides via a thermochemical method, wherein the NBFRs comprise tetrabromobisphenol A 2,3-dibromopropyl ether (TD or TBBPA-DBPE) and tetrabromobisphenol A diallyl ether (TAE or TBBPA-DAE); the Zn-based metal oxides comprise zinc oxide (ZnO) and franklinite ($ZnFe_2O_4$); and co-pyrolysis of the NBFRs with the metal oxides suppresses emission of brominated species from the NBFRs upon thermal decomposition and produces a bromine-free stream of hydrocarbons.

In an embodiment of the present invention, the ZnO is used as a metallic substrate to capture bromine free radicals during the thermal decomposition of the NBFRs, forming metal bromides comprising $ZnBr_2$.

In another embodiment of the present invention, the ZnO serves as an effective debromination agent by capturing approximately 92% of released hydrogen bromide (HBr) gas during the co-pyrolysis.

According to the present disclosure, the process wherein a thermogravimetric analysis (TGA) indicates a pyrolytic run up to 500° C. with a ramp of 10° C./min and the NBFRs treated with the ZnO produce a trivial amount of brominated compounds of approximately 0.83% relative area.

In an embodiment of the present invention, the process wherein the NBFRs treated with the ZnO produce pyrolyzed residues (pyrochar), non-condensable gases, and condensates, wherein the pyrochar retains the metal bromides comprising $ZnBr_2$, the non-condensable gases comprise inorganic gases and methane, and the condensates comprise phenol and the trivial amount of brominated compounds.

In an embodiment of the present invention, the bromine-free stream of hydrocarbons comprises the phenol as a condensable product formed by the β-scission debromination reaction from the parental molecular skeleton, and the methane gas.

In an embodiment of the present invention, the process wherein ion chromatography (IC) analysis demonstrates a low emission of less than 8% of the HBr gas during the ZnO treatment, due to the capture of the bromine free radicals into the $ZnBr_2$.

In another embodiment of the present invention, FT-IR gas analysis confirms that no HBr is generated during the ZnO treatment, validating the capture of bromine by the ZnO.

In an embodiment of the present invention, pyrochar analysis confirms the presence of the metal bromides retained in the residue, averting bromine release and indicates the presence of unused catalysts amidst the metal bromides.

In another embodiment of the present invention, ZnO also serves as a universal dehalogenation additive capable of simultaneously capturing halogens comprising fluorine, chlorine, and bromine.

In an embodiment of the present invention, the process wherein the Zn-based metal oxides are sourced from electrical arc furnace dust (EAFD), and the metal oxides convert into their respective metal bromides during the co-pyrolysis, enabling selective extraction of zinc from the EAFD.

In another embodiment of the present invention, the process enables the use of spinel ferrites other than franklinite, comprising cuprospinel ($CuFe_2O_4$), trevorite ($NiFe_2O_4$) or cobalt ferrite ($CoFe_2O_4$) for the debromination of the NBFRs.

There is disclosed a thermochemical method for debromination of novel-brominated flame retardants (NBFRs) using Zn-based metal oxides comprising: mixing the NBFRs comprising tetrabromobisphenol A 2,3-dibromopropyl ether (TD or TBBPA-DBPE) and tetrabromobisphenol A diallyl ether (TAE or TBBPA-DAE) with the Zn-based metal oxides comprising zinc oxide (ZnO) and franklinite ($ZnFe_2O_4$); subjecting the mixture to co-pyrolysis in a thermal reactor; capturing bromine radicals to form metal bromides, thereby restricting emission of brominated species from the NBFRs; and recovering bromine-free hydrocarbons.

In an embodiment of the present invention, thermochemical method further comprising an ice trap downstream of the thermal reactor to collect condensable fractions and a sodium wash trap to collect non-condensable fractions.

According to the present invention, the ZnO captures bromine radicals into metal bromides during the thermal decomposition of the NBFRs and serves as an effective debromination agent by achieving approximately 92% capture of hydrogen bromide (HBr) gas during the co-pyrolysis.

In another embodiment of the present invention, thermogravimetric analysis (TGA) indicating a pyrolytic run up to 500° C. with a ramp of 10° C./min and the NBFRs treated with the ZnO produce a trivial amount of brominated compounds of approximately 0.83% relative area.

According to the present invention, the method wherein NBFRs treated with the ZnO produce pyrolyzed residues (pyrochar), non-condensable gases and condensates, wherein the pyrochar retains the metal bromides comprising $ZnBr_2$, the non-condensable gases comprise inorganic gases and methane, and the condensates comprise phenol and the trivial amount of brominated compounds.

In an embodiment of the present invention, the bromine-free hydrocarbons comprise the phenol as a condensable product formed by the β-scission debromination reaction from the parental molecular skeleton, and the methane gas.

In an embodiment of the present invention, ion chromatography (IC) analysis demonstrates a low emission of less than 8% of the HBr gas during the ZnO treatment, due to the capture of the bromine radicals into the $ZnBr_2$ and further validated by FT-IR gas analysis.

In another embodiment of the present invention, the Zn-based metal oxides for the thermochemical method are sourced from electrical arc furnace dust (EAFD) and the metal oxides convert into their respective metal bromides during the co-pyrolysis, enabling selective extraction of zinc from the EAFD.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

DETAILED DESCRIPTION OF THE INVENTION

The aspects of the proposed debromination process and method for the novel BFRs using zinc-based additives—according to the present invention will be described in conjunction with FIGS. 1-6. In the Detailed Description, reference is made to the accompanying figures, which form a part hereof, and which is shown by way of illustration specific embodiments by which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

The present invention proposes debromination of novel brominated flame retardants (NBFRs) using Zn-based additives as a viable thermochemical approach to completely restrict the release of bromine into the atmosphere during thermal decomposition and to produce bromine-free stream of hydrocarbons. Co-pyrolysis of BFRs with metal oxides is introduced as a potent chemical recycling method that produces bromine-free hydrocarbons. The proposed solution focuses on the debromination of two prominent NBFRs: tetrabromobisphenol A 2,3-dibromopropyl ether (known as TD or TBBPA-DBPE) and tetrabromobisphenol A diallyl ether (TAE or TBBPA-DAE) through their co-pyrolysis with zinc oxide, also known as zincite (ZnO), and franklinite ($ZnFe_2O_4$). Most of the zinc content in electrical arc furnace dust (EAFD) exists in the form of these two metal oxides. Converting these oxides into their respective bromides can also facilitate the selective extraction of valuable zinc content from EAFD. The debromination potential of both oxides is evaluated through comprehensive characterization studies, analysing the generated products including char, gas, and condensates. The disclosed invention proposes ZnO as an effective debromination agent for NBFRs, demonstrating a high efficiency in capturing bromine at 92%. The solution facilitates environmentally friendly thermal treatment of e-waste containing NBFRs, utilizing ZnO for effective bromine capture.

According to the disclosure, the thermogravimetric analysis (TGA) suggests a pyrolysis run up to 500° C. The TAE (TBBPA-DAE) treatment with ZnO results in only a trivial amount of brominated compounds (relative area, 0.83%). Phenol is the sole common compound found in the condensable products, potentially formed by the β-scission debromination reaction from the parental molecular skeleton. Inorganic compounds and methane are generated as the major constituents in the gaseous products. Analysis of the pyrochar confirm the presence of metal bromides retained in the residue, preventing the release of bromine into the atmosphere. Ion chromatography (IC) analysis shows that less than 8% of hydrogen bromide (HBr) gas is released into the atmosphere upon co-pyrolysis with ZnO. The solution presented herein also suggests the use of other spinel ferrites in combating brominated polymers, envisaged by the dominating effectiveness of ZnO in debrominating NBFRs. Additionally, in practical scenarios, brominated plastics often coexist with other halogen entities like PVC and perfluorinated chemicals and ZnO can be considered as a universal dehalogenation additive capable of simultaneously capturing the three categories of halogens: fluorine, chlorine, and bromine.

Brominated flame retardants (BFRs) are bromine-bearing additives that are integrated into polymeric fraction in various applications to prevent fire ignition. Following the prohibition of legacy BFRs usage by the Stockholm Convention and various other legislations, novel BFRs (NBFRs) are introduced into the market as an alternative to the legacy BFRs. The electrical and electronics industry has witnessed substantial adoption of NBFRs. Post Stockholm Convention (2004), and the subsequent transition from legacy BFR to NBFRs, the production of TBBPA-DAE in Europe was reported to be 1-10 tons and in the US to be <453 tons in 2018. Their prevalent dispersal into the environment, the deleterious impacts and the potential neurotoxicity pose a significant threat to human health. Recent studies have detected NBFRs in household dust, aquifers and various aquatic and aerial species, underscoring environmental concerns. The brominated polymers contained in the e-waste restricts its recycling provisions via conventional thermal treatment technique as they emit toxic hydrogen bromide (HBr) gas and polybrominated dibenzo-p-dioxins and furans (PBDD/Fs) during open incinerations. PBDD/Fs are considered toxic persistent organic pollutants (POPs) exhibiting similar or higher toxicities than the notorious dioxins. Prior to this invention, no thermal studies have investigated the treatment of ZnO on NBFRs. This invention realizes the best viable solution till date for an effective and environmentally friendly thermal treatment using ZnO, to manage the ever-increasing loads of e-waste laden with novel brominated fire retardants (NBFRs). The debromination efficacy of ZnO upon novel BFRs has been revealed with good efficiency in HBr capture.

The significance of the invention lies in its ability to utilize ZnO in the co-pyrolysis process with novel BFRs, achieving complete elimination of PBDD/Fs and capturing approximately 92% of HBr gas. It presents numerous benefits. It has the potential to serve as a cutting-edge technology for the management of different types of waste amassing worldwide including e-waste and Zn-based waste. ZnO also serves as a universal dehalogenation additive used to captures the three categories of halogens of fluorine, chlorine, and bromine in scenarios where, brominated plastics co-exist with halogen entities such as PVC and perfluorinated chemicals. Probes into leaching or recovering valuable metals from the resultant pyrochar, as a further embodiment of the proposed invention, could apprehend significant financial benefits. Pyrochar, which is a biochar derived from high-temperature pyrolysis, has demonstrated its effectiveness as a valuable soil amendment and research indicates that its application can effectively sustain soil nutrient levels as well. The findings herein secure the feasibility of scaling up the invention to a larger operational scale.

Transition metals, with their partially filled d-orbitals, facilitate electron exchange in any catalytic reactions, exhibiting multiple oxidation states. The use of different metallic oxides of transition metals as halogen scavengers during co-pyrolysis with brominated polymers has been reported. Complete restriction of bromine release into the atmosphere during the thermal decomposition of TBBPA is achieved using zinc metal oxides. Herein, ZnO has been used as the metallic substrate to capture bromine free radicals during the thermal degradation of the novel BFRs. Franklinite (ZnFe2O4) and zincite (ZnO) are the major constituents in electric arc furnace dust (EAFD). Franklinite ($ZnFe_2O_4$), a major component (40.4 wt %) of EAFD is a zinc ferrite mineral from the spinel group and is considered a prime source of zinc, trailed by zincite (ZnO). At elevated temperatures, zinc ferrite converts to zincite (ZnO). Since it has access to both transition metals, according to recent investigations, its dehalogenation efficiency during pyrolysis demonstrated that the onset temperature of dehydrochlorination in PVC was reduced by 37° C. due to the presence of franklinite. Therefore, zinc metal oxides can be employed as a universal dehalogenation additive for halogen capture as well. A leaching approach to extract zinc from EAFD by transforming $Zn^{2+}$ ions into $ZnBr_2$ during co-pyrolysis with TBBPA, exploits the evolved hydrogen bromide (HBr) gas, which acts as an effective brominating agent.

BFRs have progressively replaced legacy BFRs, emphasizing the critical need to understand the chemical reactions underlying their decomposition during widely utilized pyrolytic catalytic upgrading operations. The proposed solution of co-pyrolysis using Zn additives fills this significant knowledge gap in managing NBFRs through disposal or treatment methods by conducting the pyrolytic or oxidative catalytic treatment specifically on these NBFRs. The disclosure aims to compare the effectiveness of ZnO and franklinite (major components of EAFD) in debrominating two typical NBFRs: Tetrabromobisphenol A 2,3-dibromopropyl ether (TD) and Tetrabromobisphenol A diallyl ether (TAE). Being the derivatives of widely used legacy BFRs, TD and TAE are known to be present in various environmental matrices and have documented toxic effects on aquatic and aerial organisms. The solution disclosed herein, focuses on three main objectives, reflecting the need to safely capture the bromine content in NBFRs: (i) identifying the temperature intervals at which NBFRs/Zn-oxides degrade, (ii) assessing the capacity/efficacy of prominent Zn-based metal oxides as debromination agents for NBFRs, and (iii) analysing the thermal decomposition products during the co-pyrolysis of TD and TAE with zinc-based additives.

In an embodiment of the invention, the novel BFRs are subjected to debromination using ZnO and franklinite. The selected novel BFRs, TD and TAE, are manually mixed with ZnO and franklinite separately according to their respective stoichiometry, assuming bromine atoms present in each novel BFR would be completely released upon thermal treatment to form the respective metal bromides. After preparing the mixtures according to the stoichiometric mass ratio, 1.5 g of the sample is subjected to pyrolysis. Prior to the co-pyrolytic runs, TGA is carried out for each mixture to determine their thermal degradation temperature window. Results from TGA guide the pyrolytic runs in the flow reactor. The reactor is purged with nitrogen gas at 100 mL/min for 10 minutes to ensure an inert atmosphere inside the reactor beforehand. The flow is 100 mL/min during the co-pyrolytic treatments as well, considering the residence time of the products in the heating zone. Once the products leave the heating zone of the reactor, a heating cord maintained at 250° C. ensures that there is no condensation or undesirable monomer formations occur on the reactor walls downstream before they reach an ice trap. The ice trap downstream captures all the condensable fractions of the products formed. The non-condensable gases flowing out of the ice trap are passed through a sodium wash trap containing 100 mL $Na_2CO_3/NaHCO_3$ solution for arresting the generated HBr (if any). The gases are then collected in a 1 L Tedlar bag and taken for product analysis in gas chromatography-mass spectrometry (GCMS) and Fourier-transform infrared (FT-IR) gas analysis. The reactor temperature is ramped at 10° C./min until it reaches the desired temperature, maintaining an isothermal stage of 10 minutes each for 200° C., 300° C., 400° C., and 500° C. Both the condensable and non-condensable fractions are collected at each isothermal stage and taken for subsequent product analysis in GCMS. The emitted HBr gas captured in the sodium wash bottle is taken for quantification in Ion chromatography (IC) analysis. The pyrochar obtained after the co-pyrolytic experiments is sent for X-ray diffraction (XRD), FT-IR, and scanning electron microscopy with energy-dispersive X-ray spectroscopy (SEM-EDX) analyses.

In another embodiment of the invention, the potential of both oxides in combating the emission of brominated species from the thermal decomposition of novel BFRs is investigated by characterization of the products generated in the process in the form of gases, condensates and pyrochar. The non-condensable gases consist of inorganic gases and methane, while the condensable fraction contains a fair amount of phenol and a lower amount of brominated compounds during the ZnO treatment producing only a trivial amount (relative area, 0.83%) at 500° C. Analyses of the pyrochar show the presence of unused catalysts amidst the metal bromides formed. $ZnBr_2$ is present in the pyrochar of the ZnO-treated novel BFR. FT-IR gas analysis confirms that no HBr is generated during the ZnO treatment, validating the bromine capture by ZnO. IC analysis demonstrates that the ZnO treatment exhibits lower emission (<8%) of HBr gas, as bromine free radicals formed during thermal decomposition are captured to form $ZnBr_2$. Condensate analysis, pyrochar analyses, and the captured HBr analysis collectively endorse ZnO as an effective debromination agent. In practical scenarios, such as municipal waste incinerators, brominated plastics are likely to coexist with other halogen entities like PVC and perfluorinated chemicals and ZnO can be considered as a universal dehalogenation additive capable of simultaneously capturing the three categories of halogens: fluorine, chlorine, and bromine.

The proposed solution of co-pyrolysis of NBFRs using zinc metal oxides offers numerous advantages and practical applications. It enables the design of an efficient chemical recycling facility for NBFRs and enhances the selective extraction of zinc from EAFD waste produced by steel industries, smelters, and similar entities. EAFD is an industrial waste facing disposal challenges which is generated in huge quantities. This approach serves as a dual solution for managing two significant waste streams: e-waste and Zn-based industrial waste, making it valuable for waste recycling companies and EAFD generators. Additionally, it can be implemented in municipal waste incinerators, where brominated plastics often coexist with other halogen-containing materials like PVC and perfluorinated chemicals.

ZnO functions as both a debrominating agent and a universal dehalogenation additive, capable of capturing fluorine, chlorine, and bromine simultaneously. Furthermore, valuable metals can be leached from the pyrochar, offering financial benefits. This invention can also be scaled up feasibly to a larger operational level, facilitated by conducting kinetic and thermodynamic analyses.

In an embodiment of the invention, an experimental set up for co-pyrolysis using Zn-based additives is implemented as a viable thermochemical approach to debrominate novel brominated flate retardants (NBFRs). The materials used include: nitrogen gas with 99.9992% purity for pyrolysis and thermogravimetric analysis (TGA), helium gas with 99.9995% ultra-high purity for the gas chromatography-mass spectrometry (GCMS) carrier gas, Tetrabromobisphenol A 2,3-dibromo-propyl ether (TD) with a chemical formula $C_{21}H_{20}Br_8O_2$, purity >95.0% with CAS #21850-44-2, commonly known as TBBPA-DBPE, and Tetrabromobisphenol A diallyl ether (TAE) with a chemical formula $C_{21}H_{20}Br_4O_2$, purity >99.0% with CAS #25327-89-3, commonly named as TBBPA-DAE. TD and TAE serve as the selected NBRFs. Zinc-based additives to be used as debrominating agents include Zinc oxide (ZnO) nanopowder (99.9% purity) with CAS #1314-13-2 and Franklinite, commonly known as Zinc iron oxide (chemical formula $Fe_2O_4Zn$) with 99% purity and CAS #12063-19-3. The experimental set up employs a horizontal plug flow reactor, and a heating cord is used to prevent condensation of products prior to analysis. Dionex™ AS23 eluent concentrate 4.5 mM sodium carbonate/0.8 mM sodium bicarbonate ($Na_2CO_3/NaHCO_3$) solution is used for ion chromatography runs; the same solution is used for sodium wash. Spectroscopic grade potassium bromide (KBr) is utilized to acquire the FT-IR spectrum.

In one embodiment of the invention, a co-pyrolysis experiment is conducted wherein the selected novel brominated flame retardants (NBFRs), specifically Tetrabromobisphenol A 2,3-dibromo-propyl ether (TD) and Tetrabromobisphenol A diallyl ether (TAE), are manually mixed with zinc oxide (ZnO) and franklinite ($ZnFe_2O_4$) separately according to their respective stoichiometric ratios. It is assumed that the bromine atoms present in each NBFR would be completely released during thermal treatment, forming the respective metal bromides. As such, this preparation results in four samples: TD:ZnO, TD:$ZnFe_2O_4$, TAE:ZnO and TAE:$ZnFe_2O_4$. After preparing the mixtures in the correct stoichiometric mass ratios, 1.5 grams of each sample is subjected to pyrolysis. Before the co-pyrolysis runs, thermogravimetric analysis (TGA) is performed on each mixture to determine their thermal degradation temperature window and the TGA results guide the subsequent pyrolytic runs in the flow reactor. The reactor is purged with nitrogen gas at a flow rate of 100 mL/min for 10 minutes to ensure an inert atmosphere inside the reactor prior to co-pyrolytic runs. This flow rate is maintained during the co-pyrolysis treatments as well considering the residence time of the products in the heating zone. As the products exit the heating zone of the reactor, a heating cord maintained at 250° C. prevents condensation or undesirable monomer formations on the reactor walls before they reach an ice trap downstream. The ice trap captures all the condensable fractions of the products formed. The non-condensable gases flowing out of the ice trap are directed through a sodium wash trap containing 100 mL of $Na_2CO_3/NaHCO_3$ solution for arresting any generated HBr.

In another embodiment of the invention, various characterization techniques are deployed to analyze the products generated after the pyrolytic process. The gases formed are then collected in a 1 L Tedlar bag for product analysis via gas chromatography-mass spectrometry (GCMS) and Fourier-transform infrared (FT-IR) gas analysis. The reactor temperature is ramped at 10° C./min until it reaches the desired temperatures, maintaining an isothermal stages of 10 minutes each at 200° C., 300° C., 400° C., and 500° C. Both condensable and non-condensable fractions are collected at each isothermal stage and analyzed using GCMS. The emitted HBr gas captured in the sodium wash bottle is quantified via ion chromatography (IC) analysis. The pyrochar obtained after the co-pyrolysis experiments is analyzed using X-ray diffraction (XRD), FT-IR, and scanning electron microscopy with energy-dispersive X-ray spectroscopy (SEM-EDX).

Figure 1:
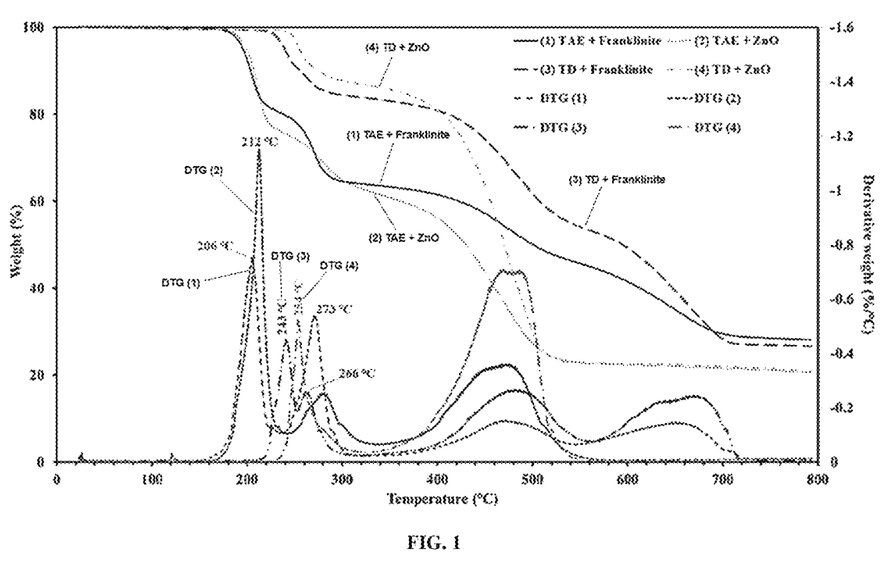
FIG. 1 shows thermogravimetric analysis (TGA) of all the samples from room temperature to 800° C.

In an embodiment of the invention, the thermogravimetric analysis (TGA) is is performed separately for the four samples TD: ZnO, TD: $ZnFe_2O_4$, TAE:ZnO and TAE: $ZnFe_2O_4$ before conducting the co-pyrolytic experiments. TGA is carried out at a heating rate of 10° C./min from room temperature to 800° C. FIG. 1 represents the thermogravimetric analysis of all the samples from room temperature to 800° C. From the figure, it is evident that the disintegration of TAE initiates at approximately 170° C. (~170° C.), while TD starts disintegrating at around 220° C. (~220° C.) in both treatments. This difference is likely due to the additional bond energy of two C—Br bonds and a C—C bond in TD, as opposed to a single terminal C=C bond in TAE. During ZnO treatment in both cases, thermal disintegration ceases at 500° C. with two degradation zones: the first zone extends between 170° C.-220° C., with a peak degradation temperature ($T_d$) of 212° C. for TAE, and the second zone extends between 420° C.-500° C. For TD, the first degradation zone is located between 220° C.-300° C., and the second zone occurs between 400° C.-500° C., with a $T_d$ of 254° C. In contrast, during the franklinite treatment, thermal disintegration ceases at 700° C. and exhibits three degradation zones. For TAE, the three observed degradation steps are located between 170° C.-280° C., 420° C.-500° C., and 520° C.-700° C., with $T_d$ values of 206° C. and 273° C. For TD, the three degradation zones occur between 220° C.-300° C., 420° C.-520° C., and 580° C.-700° C., with $T_d$ values of 243° C. and 266° C.

In all cases, the first zone signifies the debromination zone, releasing HBr gases. At this stage, the metallic cations start capturing the bromine free radicals to form the respective metal bromides, as validated in subsequent XRD and SEM-EDX analyses. The second degradation zone in ZnO treatment is related to carbothermic reduction reactions, producing CO and $CO_2$. In franklinite treatment, direct bromine elimination leads to the unstable $FeBr_3$ eventually being converted to $FeBr_2$ during the second stage. As the formed $ZnBr_2$ melts beyond 402° C. and reacts with hematite to form franklinite, further weight loss occurs in the second stage. The third degradation zone in franklinite treatment indicates the gradual evaporation of $FeBr_2$ at temperatures above 540° C., which can also be related to carbothermic reduction reactions producing CO and CH4. Both NBFRs decompose completely by 500° C. during ZnO treatment, and beyond this temperature, $ZnBr_2$ vaporizes. Although NBFRs degradation ceases at 700° C. during franklinite treatment, after the complete conversion of $ZnBr_2$ to franklinite, $FeBr_2$ starts vaporization. It is to be noted that pyrolysis is conducted until 500° C. as the aim is to control the release of bromine release into the atmosphere and retain the metal bromides in the pyrochar.

Figure 2:
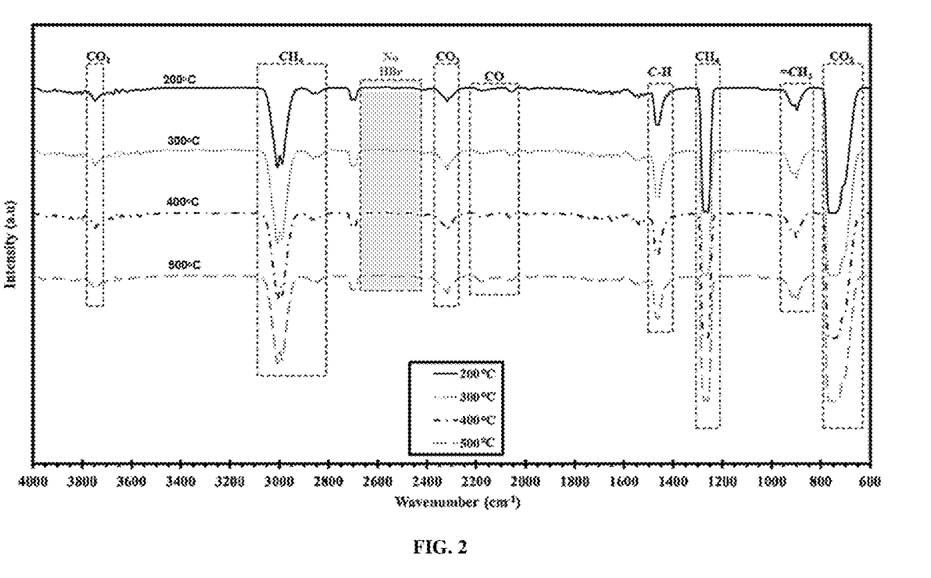
FIG. 2 shows Fourier-transform infrared (FT-IR) analysis of the emitted gases during the tetrabromobisphenol A diallyl ether (TAE) treatment with franklinite.

In another embodiment of the given disclosure, the decomposition products of novel brominated flame retardants (NBFRs) after co-pyrolytic treatment with franklinite and ZnO are subjected to qualitative analysis. The analysis involves gas chromatography-mass spectrometry (GCMS) analysis and covers both condensable and non-condensable fractions at different temperatures. The gaseous products from the disintegration of TAE during its co-pyrolysis with franklinite and ZnO are predominantly inorganic gases and methane ($CH_4$), with minimal/trivial organic compounds, as it is a polymeric degradation. Whereas the emerging gaseous products from TD degradation constitute phenols and n-hexadecanoic acid in traces, produced via homolytic β-scission of $C_{aromatic}$—C bonds. In an embodiment of the current invention, the gaseous products in all four cases are subjected to FT-IR gas analysis at all temperature ranges and the major contributors to these gaseous products in all the cases, are identified as inorganic gases and $CH_4$. FIG. 2 represents the FT-IR analysis of the emitted gases during the TAE treatment with franklinite. The peaks of $CO_2$ are evident from the vibrations around 2350-2250 $cm^{-1}$, 800-650 $cm^{-1}$, and at 3750 $cm^{-1}$. Carbon monoxide (CO) stretching peaks, observed from 2200 to 2000 $cm^{-1}$, show extremely low intensity as its production is scanty. However, methane production is significant compared to ethylene gas ($H_2C=CH_2$), with stretching peaks formed at around 3000 $cm^{-1}$ and 1250 $cm^{-1}$ for $CH_4$ and around 900 $cm^{-1}$ for ethylene. The syngas generated can be harnessed using cobalt-based nano-catalysts via the Fischer-Tropsch process into paraffin and olefins. No HBr peaks are detected at 2650-2400 $cm^{-1}$, as previously reported during the legacy BFR degradation, indicating effective bromine capture by the sodium wash.

All four cases produce similar gas peaks at all temperatures, with trivial intensity differences during FT-IR gas analysis. Table 1 tabulates the condensable products emerged during the TAE co-pyrolysis with ZnO with respect to the retention time. The condensable products collected in the ice trap, as detailed in Table 1, are mainly constituted of compounds comprising phenol, bromophenols, and dibromophenols. 2,6-Dibromophenol is formed through homolytic scission of the $C_{aromatic}$—C bonds from the parental molecular skeleton. Further debromination via β-scission produces 2-bromophenol and phenols. As observed for legacy BFRs, benzofurans and dioxins also emerge during the TAE decomposition in both treatments, with a relative area >10% at lower temperature ranges. Nevertheless, phenol and paraffin formation at higher temperatures eventually eliminates the formation of dioxins and furans during co-pyrolysis with ZnO. However, an exception is noted for dioxin residing at 3.05% even at 500° C. when TAE is treated with franklinite. Due to the higher (double) bromine content in TD, its decomposition products have a higher brominated content than TAE's, resulting in negligible dioxin and furan production at even lower temperature ranges. Unlike the franklinite treatment, TAE with ZnO treatment produces n-alkanes such as octane, hexadecane, and octadecane. While TD produces only trace alkanes at higher temperatures when co-pyrolyzed with franklinite, the TAE co-pyrolysed with ZnO treatment is able to produce alkanes at all temperature ranges. A similar trend is also observed when TD is co-pyrolyzed with $Ca(OH)_2$ reported in previous works. Co-pyrolysis of TAE with ZnO produces alkanes at 53.01% at 200° C., 52.25% at 300° C., and 59.48% at 400° C., but this reduces to 29.34% at 500° C. as more phenol (21.07%) and methallyl butyrate (30.66%) are produced therein.

TABLE 1

Condensable products emerged during the TAE co-pyrolysis with ZnO w.r.t the retention time

| Compounds | Retention time (R2) | Peak relative area (%) | | | |
|---|---|---|---|---|---|
| | | 200oC | 300oC | 400oC | 500oC |
| Methallyl butyrate | 2.125 | — | — | — | 30.66 |
| 2-methyl-Propanoic acid anhydride | 2.177 | — | 6.33 | 8.67 | — |
| 2,3,4-trimethyl-Hexane | 2.509 | — | — | — | 10.42 |
| Phenol | 4.231 | 15.16 | 9.15 | 16.48 | 21.07 |
| 2-bromo-Phenol | 5.249 | 6.24 | — | — | — |
| 2-methyl-Benzofuran | 5.665 | 10.78 | 4.04 | — | — |
| Octane | 6.481 | — | — | — | 12.09 |
| 2-(1-pentenyl)-Furan-(Z) | 6.696 | 1.71 | — | — | — |
| 2-propyl-Phenol | 6.698 | — | 1.36 | — | — |
| 2-(1-methylethyl)-Phenol | 6.745 | — | 1.79 | — | — |
| 2,4-dibromo-Phenol | 7.981 | — | 1.72 | — | — |
| 2,6-dibromo-Phenol | 8.276 | — | 1.81 | — | — |
| 2-bromo-2,3-dihydro-1H-Inden-1-ol | 8.571 | 4.53 | 6.81 | — | — |
| 1-bromo-3-(2-propenyloxy)-Benzene | 8.573 | — | 1.75 | 2.36 | 0.35 |
| Hexadecane | 9.987 | 53.01 | 31.16 | 59.48 | — |
| 1-(3,5-Dibromo-4-hydroxyphenyl)ethanone | 10.428 | — | 4.65 | 3.63 | 0.48 |
| Octadecane | 11.475 | — | 21.09 | — | 17.25 |
| Other miscellaneous | — | 8.57 | 8.34 | 9.38 | 7.68 |

Figure 3A:
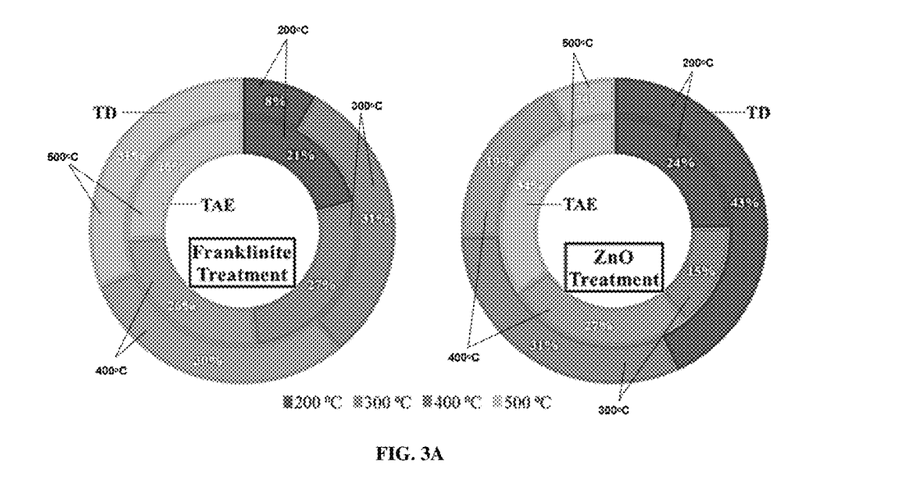
FIG. 3A shows the comparison chart (normalized percentage) for the phenol production.
Figure 3B:
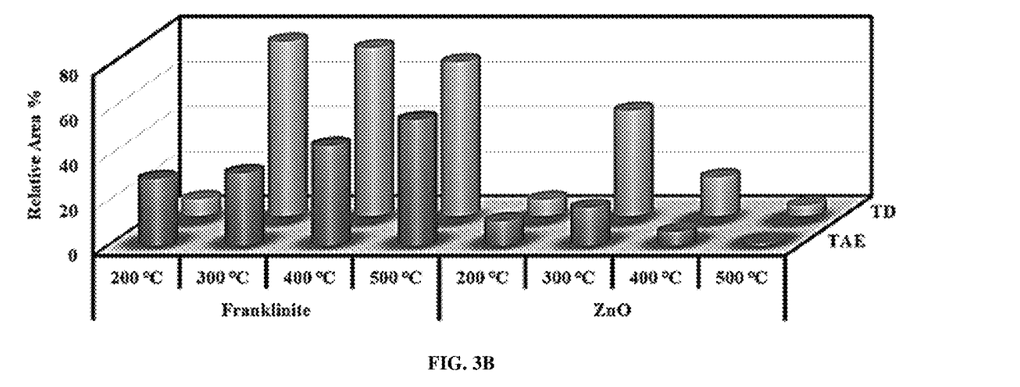
FIG. 3B shows the brominated compounds identified in the condensate during the four studies.

FIG. 3A shows the comparison chart (normalized percentage) for the phenol production. As shown in the figure, franklinite treatment increases the relative area of phenol by 26% for TAE, whereas ZnO treatment increases it by 39%. During TD decomposition, phenol increases 3.87 times over the same temperature range with franklinite, but ZnO treatment reduces the relative area of phenol by 84%. Phenols can be further decomposed by oxidation techniques or innovative nanocatalytic sono-fenton processes. The two-fold bromine atoms in TD as compared to TAE, lead to the persistent formation of brominated compounds during its degradation. FIG. 3B shows the brominated compounds identified in the condensate during the four experiments. FIG. 3B illustrates that ZnO treatment is more effective in bromine capture compared to franklinite. At 200° C., TAE produces more brominated compounds than TD with franklinite treatment because TD disintegration triggers after TAE at approximately ~220° C. only. The brominated compounds from TAE decomposition increase progressively, by 8.84% at 300° C., 37.8% at 400° C., 26% at 500° C., and stays at 55.81%. Conversely, TD decomposition, though very low brominated compounds emanated at 200° C., shows a hike up to 10.6 times in brominated compounds at 300° C., fand exhibits a gradual reduction by 4% at 400° C. followed by 8.6% reduction at 500° C. and stays at 68.26%. Similar to the de-chlorination study disclosed earlier, franklinite is less effective in bromine capture, while ZnO treatment generates fewer brominated compounds as obvious from FIG. 3B.

ZnO treatment portrays a sheer performance for TAE decomposition and effectively reduces the brominated compounds from TAE to a trivial amount (0.83%) at 500° C. From 200° C., though it increases slightly by 55% at 300° C., the brominated compounds decline drastically by 64% at 400° C. and stoops again by 86% at 500° C. For TD, since its decomposition initiates only after 200° C., the brominated compounds stands at 46.74% at 300° C. which can be attributed to the presence of double the amount of bromine as compared to TAE. The brominated compounds decrease dramatically by 63% at 400° C. and further diminishes by 73% at 500° C. Increasing the temperatures release more free bromine radicals, which are captured by metallic zinc, and hence forming zinc bromide ($ZnBr_2$) at higher temperatures, during the ZnO treatment for both TAE and TD. The condensed fragments can be further treated with an emulsion liquid membrane for the recovery of metals, phenols, and other organic compounds.

In one embodiment of the proposed solution, a solid residue analysis is performed and further involves a spectral analysis. The pyrochar obtained from the experiments is subjected to infrared (IR) spectral analysis to identify the functional groups enduring in the char. The fingerprint region (1500-400 $cm^{-1}$) shows meager peaks of a typical char with less dominant peaks, except for the treatment of TD.

According to the spectral analysis results, pure ZnO generates a sharp transmittance band from 420 to 559 $cm^{-1}$, conforming to the Zn—O stretching modes. Broad and short transmittance peaks around 900 $cm^{-1}$ and 1400 $cm^{-1}$ also align with Zn—O stretching. Pure franklinite displays two typical absorption peaks, characteristic of a spinel ferrite, at $v_1$(571-547 $cm^{-1}$) corresponding to the vibrational frequencies due to the cation-oxygen interactions at the tetrahedral site ($M_{actra}$-O) pertaining to Fe—O bond and $v_1$ (447-432 $cm^{-1}$) due to metal oxide interactions at the octahedral site ($M_{octa}$-O) pertaining to Zn—O bond.

For the TAE treatment with ZnO, the pyrochar obtained generates no significant peaks other than a generic ZnO peak with lower intensity at 440 $cm^{-1}$. Similarly, the TAE treatment with franklinite also produces no peaks other than only a very low-intensity peak of spinel ferrite. However, during the TD treatment with ZnO, short Zn—O stretching vibrations at 559 $cm^{-1}$ are observed, along with short rocking vibrations of $CH_3$ at 1162 $cm^{-1}$ and short C=C aromatic stretching vibrations at 1610 $cm^{-1}$ sustained.

In the TD treatment with franklinite, after the typical spinel ferrite peaks at the $v_1$ and $v_2$ regions, a sharp peak at 619 $cm^{-1}$ indicates aromatic C—Br stretching vibrations. Peaks from 690 to 900 $cm^{-1}$ correspond to =CH aromatic bending, and a small peak at 980 $cm^{-1}$ is associated with strong C=C bending. Additionally, short rocking vibrations of $CH_3$ at 1162 $cm^{-1}$ are observed. A broad, low-intensity peak around 3400 $cm^{-1}$ corresponds to any —OH stretching vibrations that may have likely intruded from atmospheric moist impurities.

Metallic halide bond vibrations typically occur in the far-IR region (400-100 $cm^{-1}$), with Fe—Br bond vibrations usually appearing in the low range of 266-244 $cm^{-1}$ and Zn—Br bond vibrations even lower at 250-200 $cm^{-1}$. Although the generated metal bromides are present in the pyrochar, they can not be identified due to the experiment's limitation to mid-IR spectral analysis. However, the pyrochar obtained from TAE during both treatments does not generate typical hydrocarbon peaks, whereas the pyrochar from TD reveals the peaks or presence of hydrocarbons retained in the char. The distinguishing peaks of pure ZnO and pure franklinite, confirm the presence of leftover catalyst in the pyrochar as well.

Figure 4:
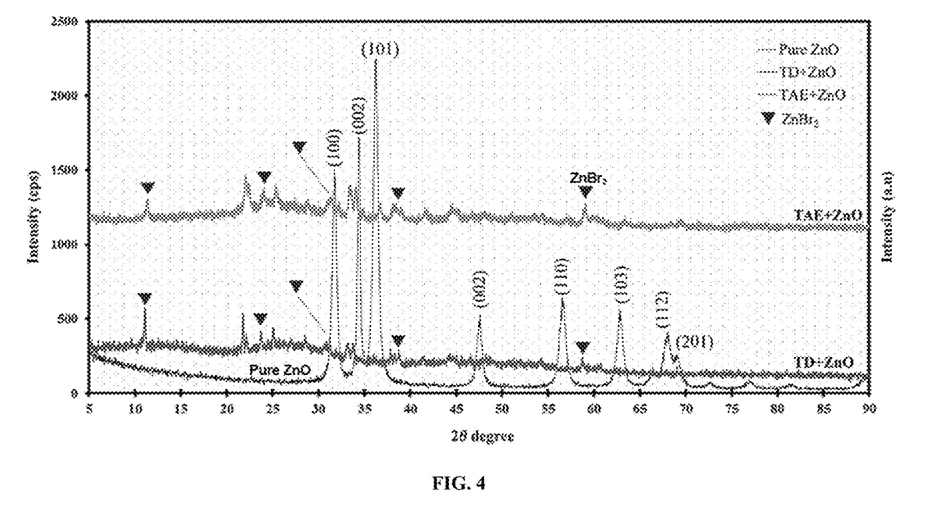
FIG. 4 shows X-ray diffraction (XRD) patterns of both pyrochars superimposed over an XRD of pure ZnO.

In another embodiment of the proposed solution, the spectral analysis involves X-ray diffraction (XRD) analysis of the solid residue left after pyrolysis. XRD analysis is deployed specifically to validate the presence of metal bromides in the pyrochar obtained from the four thermal treatments. The crystalline phases present in the pyrochar are identified and compared with the respective catalysts. FIG. 4 shows the XRD patterns of pyrochars formed from both the NBFRs treated with ZnO, superimposed over an XRD of pure ZnO, in which the diffraction peaks of pure ZnO (primary axis) are used as a backdrop to overlay the diffraction peaks of pyrochars formed from both the NBFRs during ZnO treatment (secondary axis). The diffraction peaks corresponding to the Miller indices (100), (002), (101), (002), (110), and (103) at 2θ degrees approximately 31.8°, 34.4°, 36.3°, 47.5°, 56.7°, and 62.9°, respectively, specify the typical wurtzite structure of ZnO nanoparticles with a hexagonal crystal system according to JCPDS no. 36-1451.

The diffraction peaks of both the pyrochars exhibit a shift in peaks pertaining to $ZnBr_2$ formation, while some low-intensity peaks are retained, demonstrating the presence of unused ZnO. The identified peaks of $ZnBr_2$ in the pyrochar at approximately 12.04°, 24.21°, 31.61°, 39.56°, and 58.41° 2θ degrees belong to the trigonal omega-like crystal structure in the R-3m space group.

Similarly, the diffraction peaks of the pyrochars formed from both the NBFRs during franklinite treatment (as secondary axis) are superimposed over a backdrop of the diffraction peaks of pure franklinite (as primary axis). The diffraction peaks generated at 2θ degrees of approximately 30.28°, 35.46°, 43.16°, 56.97°, and 62.470 with crystal planes of (220), (311), (400), (511), and (440) respectively, validate the distinctive spinel ferrite face-centered cubic structure of pure $ZnFe_2O_4$ nanoparticles according to JCPDS 89-1009.

In the pyrochar for both the NBFRs, though $ZnBr_2$ is formed, it converts back to franklinite by reacting with the available hematite at high temperatures above 402° C. (by solid-liquid reaction), preventing the formation of respective peaks. However, the peaks of the formed $FeBr_2$ formed at 530 and 570 2θ degrees are not intense, which can be due to the hygroscopic nature attained by the iron bromide or due to the formation of a microcrystalline structure which is below the detection limit of XRD. Another reason can be the common diffraction peaks of the residual franklinite and iron bromide competing for the same diffraction peak, making peak identification challenging as reported in previous studies. Therefore, these samples are further subjected to SEM-EDX analysis to determine the elemental composition, which is discussed in the next section.

Figure 5:
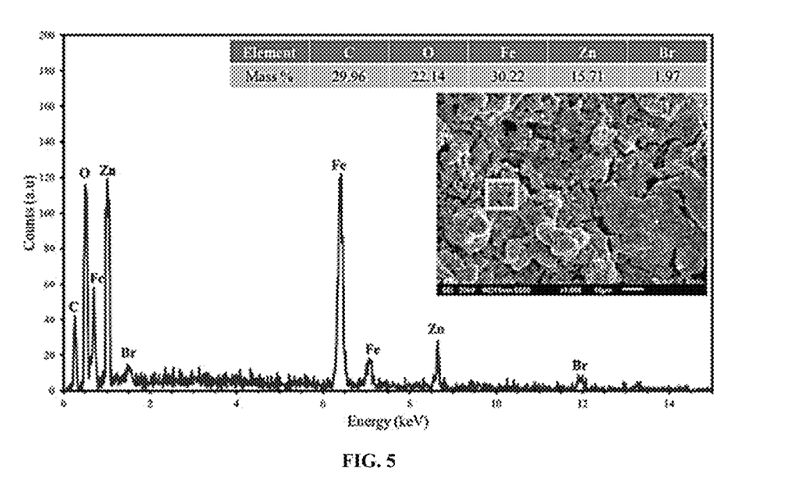
FIG. 5 shows Scanning electron microscopy with energy-dispersive X-ray spectroscopy (SEM-EDX) for the pyrochar of tetrabromobisphenol A 2,3-dibromopropyl ether (TD) with franklinite.

In another embodiment of the proposed invention, morphological analysis and elemental mapping of the solid residue after pyrolytic treatment of the selected NBFRs is carried out. As already discussed, the presence of crystalline structures of the formed $ZnBr_2$ and $FeBr_2$ is confirmed by XRD analysis, while SEM-EDX is employed to analyze the elemental composition and surface morphology of all the pyrochars. The pyrochar from TAE upon ZnO treatment, generates intergranular aggregates. The elemental mass composition of a selected area is depicted as zinc (32.22%) and bromine (9.14%) amidst carbon (43.23%) and oxygen (15.41%), confirming the presence of $ZnBr_2$ along with the remaining unused catalyst. The EDX spectral analysis generates peaks for carbon (Kα), oxygen (Kα), zinc (Lα), bromine (Lα), zinc (Kα), and bromine (Kα) at 0.277, 0.525, 1.01, 1.48, 8.63, and 11.907 keV respectively. EDX mapping of the pyrochar shows a uniform dispersal of carbon, followed by zinc and bromine. The pyrochar from the franklinite treatment of TAE displays a morphology of spherical balls of the $FeBr_2$ formations adhered to a rough surface of spent franklinite, with the mass fraction of zinc being 13.91% from the franklinite, as all the formed $ZnBr_2$ is converted back to franklinite. EDX spectra also include Lα and Kα peaks of iron at 0.705 and 6.398 keV energy levels. EDX maps out evenly distributed carbon, upon which franklinite is placed and topped up by bromides. The surface morphology of the pyrochar from TD upon ZnO treatment shows a porous Emmental cheese-like structure with scattered $ZnBr_2$ on irregular graphitic carbon flakes, along with unexploited catalysts. Both the EDX spectral analysis and elemental mapping confirm the widespread graphitic flakes with a 52.51% carbon mass fraction. However, the percentage of bromine is much lower (3.41% mass fraction), even though TD has two-fold bromine content than TAE. This reduction in $ZnBr_2$ can be attributed to the amount of brominated compounds in the condensate and the release of HBr gas, as discussed in following sections. The pyrochar of TD with franklinite treatment exhibits agglomerated morphology of diverse shapes with carbon spread over revived franklinite. FIG. 5 depicts the SEM-EDX for the pyrochar of TD with franklinite. Although the bromine mass fraction is low, the EDX spectral analysis confirms the presence of bromine (1.97%) in FIG. 5, confirming the presence of only $FeBr_2$ in the pyrochar, as all the $ZnBr_2$ is reverted to franklinite at higher temperatures. Most of the bromine released from TD accumulates in the condensate, with the rest expelled as HBr gas, making it the highest HBr producer among the four sets of experiments. EDX mapping also confirms the poor spread of bromine in the targeted mapping area, indicating inferior bromine capture competence by franklinite compared to ZnO.

Figure 6:
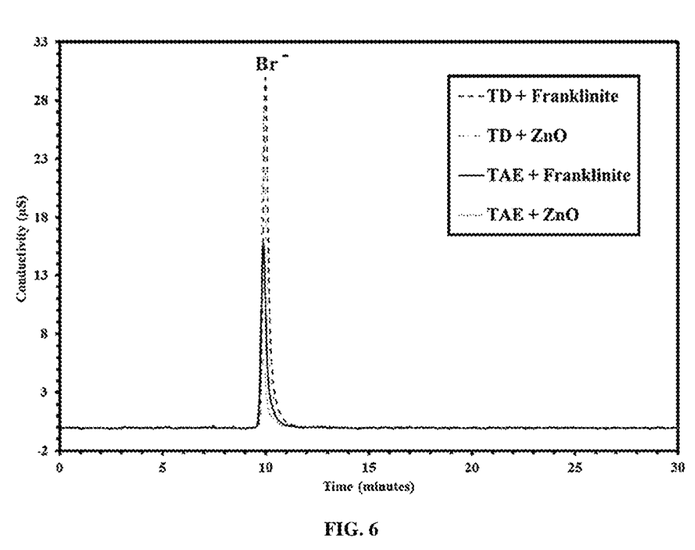
FIG. 6 shows the captured bromide peaks identified from Ion chromatography (IC) analysis.

In an embodiment of the invention, the HBr realization and its mechanistic pathway is analysed in detail. According to pertinent literature, approximately 50% by weight of the bromine is expelled as toxic HBr gas through the bimolecular abstraction reaction of free radicals of hydrogen and bromine, or by direct elimination during the thermal degradation of an NBFR. According to the proposed solution, this highly corrosive HBr gas is captured by the sodium wash ($Na_2CO_3/NaHCO_3$ solution) placed after the ice trap. Due to the strong acidic nature of HBr, it dissociates completely in an aqueous realization solution, facilitating a neutralization reaction with the $Na_2CO_3/NaHCO_3$ solution, resulting in the formation of sodium bromide (NaBr). The NaBr formed is used to quantify the HBr production by direct stoichiometry. FIG. 6 shows the captured bromide peaks identified from IC analysis. As shown in the figure, NaBr is analyzed using ion chromatography for all four experiments after three times dilutions, revealing that the HBr produced is 54.06 mg/g for the TAE treatment with ZnO, 145.86 mg/g for the TAE treatment with franklinite, 249.75 mg/g for the TD treatment with ZnO, and 275.37 mg/g for the TD treatment with franklinite. The relative increment in HBr production for TD is attributed to the double bromine presence compared to TAE. In a recent study, it is found that a significant amount (679.66 mg/g) of HBr is released from pure TBBA. Thus, it is construed that over 92% (>92%) of HBr emission is fixed by ZnO treatment for TAE. Conversely, a 78.5% reduction is observed for the TAE treatment with franklinite, a 63.2% reduction for the TD treatment with ZnO, and a 59.5% reduction for the TD treatment with franklinite. A similar trend in the organic bromine is also witnessed in the condensate, as already discussed herein in the product analysis section. Thsese reductions in the organic and inorganic bromines are due to the formation of $ZnBr_2$ (retained in the pyrochar) at higher temperatures, as validated by XRD and SEM-EDX analyses. However, franklinite cannot be fully exploited from its bimetallic potential due to multiple interactions and the comparatively lower efficiency of hematite formed at higher temperatures.

Upon molecular modeling done as previously disclosed, it is found that the non-polar ZnO(1010) surface serves as a catalytic platform for the dissociative adsorption of HBr into adsorbed H and Br atoms. This catalytic capacity of ZnO stems from the Zn—O linkage in ZnO, which serves as Lewis acid-base sites. Most involved steps incur low activation barriers when compared with the relatively strong H—Br bond in HBr, which requires 87.1 kcal/mol for uncatalyzed bond fission. Eventually, an intermediate oxybromide structure facilitates the binding of electronegatively charged $Br^-$ anions with surficial $Zn^{2+}$ cations. Simultaneous chemisorption of the charge donor hydrogen atom upon the surface oxygen atom generates a hydroxyl group, encouraging the bromine atom to trade as a Lewis acid site. This uptake of HBr by the ZnO surface is perceptible by its exothermic nature at −42.4 kcal/mol. Subsequent HBr dissociative uptakes by the ZnO surface lead to the generation of an oxybromide configuration. Intramolecular surface hydrogen transfer steps in the latter structures initially form surface hydroxyl groups followed by the desorption of water molecules. The HBr dissociative uptake governs the subsequent generation of the $ZnBr_2$ phase.

In a similar vein, the mechanistic steps and a kinetic study formulation for the interaction of HBr and small brominated hydrocarbon cuts with the franklinite surface can be presented. The $ZnFe_2O_4$ unit cell poses a typical spinel structure with $Zn^{2+}$ cations residing at the tetrahedral sites and $Fe^{2+}$ cations aligning in octahedral coordination, exposing the Zn—O bond surface and the Fe—O bond surface for hydrogen bromide surface interactions. Unlike the exothermic reactions observed over the Zn—O surface bonds, the Fe—O linkages on the $ZnFe_2O_4$(110) surface participate in the surface-assisted fission of H—Br bonds in nearly neutral reactions. Through physisorption, an HBr molecule reaches the Fe—O surface bond and dissociative adsorption occurs with a reaction barrier of 8.2 kcal/mol. Ensuing HBr addition leads to dissociative decomposition on another Fe—O bond, thus generating two hydroxyl groups that release a water molecule via endothermic (2.1 kcal/mol) intramolecular hydrogen transfer from an iron atom, with an activation barrier of 41.2 kcal/mol. This water elimination also authenticates the ferric bromide formation on the catalytic surface.

In conclusion, the potential of a bimetallic oxide over a monometallic oxide in mitigating the emission of brominated species from the thermal decomposition of NBFRs is investigated. TGA analysis, prior to co-pyrolysis, suggests a pyrolytic run up to 500° C. with a ramp rate of 10° C./min for all combinations, aiming to retain the generated metal bromides in the pyrochar. The non-condensable gases consist of inorganic gases and methane in all cases, while the condensable fraction contains a fair amount of phenol and brominated compounds. The TD treatment with franklinite generates a higher amount of brominated compounds, whereas ZnO treatment produces a lower amount. The TAE treatment with ZnO results in a trivial amount of brominated compounds (relative area, 0.83%) at 500° C. Pyrochar analysis reveals the presence of unused catalysts amidst the formed metal bromides. $ZnBr_2$ is found in the pyrochar from ZnO treatments, while only $FeBr_2$ is present in the pyrochar from franklinite treatments, as all generated $ZnBr_2$ reverts to franklinite. FT-IR gas analysis confirms that no HBr is generated, validating its capture by the sodium wash. IC analysis demonstrates that HBr production is higher for TD due to the two-fold presence of bromine compared to TAE, with ZnO treatment showing lower emission (<8%) of HBr gas as bromine free radicals formed during thermal decomposition are captured to form $ZnBr_2$. The analyses of condensate, pyrochar, and captured HBr collectively indicate that franklinite is less effective than ZnO as a debromination agent. This could be potentially due to the reverse reaction of $ZnBr_2$ with hematite above its melting point in the solid-liquid phase.

The dominance of ZnO suggests exploration into other spinel ferrites for combating brominated polymers as further embodiment of the proposed solution. In an embodiment of the invention, the debromination potential of other spinel ferrites such as cuprospinel ($CuFe_2O_4$), trevorite ($NiFe_2O_4$), or cobalt ferrite ($CoFe_2O_4$) can be investigated. The bromides of these oxides are thermally stable and can be retained at significantly higher temperatures. Additionally, in practical scenarios such as municipal waste incinerators, brominated plastics are likely to coexist with other halogen entities like PVC and perfluorinated chemicals. Therefore, as another embodiment of the invention, ZnO can be developed as a universal dehalogenation additive that simultaneously captures the three categories of halogens-fluorine, chlorine, and bromine.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims, which follow.

The invention claimed is:

1. A process for debromination of novel-brominated flame retardants (NBFRs) using Zn-based metal oxides via a thermochemical method, wherein the NBFRs comprise tetrabromobisphenol A 2,3-dibromopropyl ether (TD or TBBPA-DBPE) and tetrabromobisphenol A diallyl ether (TAE or TBBPA-DAE);
   the Zn-based metal oxides comprise zinc oxide (ZnO) and franklinite ($ZnFe_2O_4$); and
   co-pyrolysis of the NBFRs with the metal oxides suppresses emission of brominated species from the NBFRs upon thermal decomposition and produces a bromine-free stream of hydrocarbons.

2. The process of claim 1, wherein the ZnO is used as a metallic substrate to capture bromine free radicals during the thermal decomposition of the NBFRs, forming metal bromides comprising $ZnBr_2$.

3. The process of claim 2, wherein the ZnO serves as an effective debromination agent by capturing approximately 92% of released hydrogen bromide (HBr) gas during the co-pyrolysis.

4. The process of claim 3, wherein thermogravimetric analysis (TGA) indicates a pyrolytic run up to 500° C. with a ramp of 10° C./min and the NBFRs treated with the ZnO produce a trivial amount of brominated compounds of approximately 0.83% relative area.

5. The process of claim 4, wherein the NBFRs treated with the ZnO produce pyrolyzed residues (pyrochar), non-condensable gases, and condensates, wherein the pyrochar retains the metal bromides comprising $ZnBr_2$, the non-condensable gases comprise inorganic gases and methane, and the condensates comprise phenol and the trivial amount of brominated compounds.

6. The process of claim 5, wherein the bromine-free stream of hydrocarbons comprises the phenol as a condensable product formed by the β-scission debromination reaction from the parental molecular skeleton, and the methane gas.

7. The process of claim 6, wherein ion chromatography (IC) analysis demonstrates a low emission of less than 8% of the HBr gas during the ZnO treatment, due to the capture of the bromine free radicals into the $ZnBr_2$.

8. The process of claim 7, wherein FT-IR gas analysis confirms that no HBr is generated during the ZnO treatment, validating the capture of bromine by the ZnO.

9. The process of claim 8, wherein pyrochar analysis confirms the presence of the metal bromides retained in the residue, averting bromine release and indicates the presence of unused catalysts amidst the metal bromides.

10. The process of claim 9, wherein ZnO also serves as a universal dehalogenation additive capable of simultaneously capturing halogens comprising fluorine, chlorine, and bromine.

11. The process of claim 10, wherein the Zn-based metal oxides are sourced from electrical arc furnace dust (EAFD), and the metal oxides convert into their respective metal bromides during the co-pyrolysis, enabling selective extraction of zinc from the EAFD.

12. The process of claim 11, wherein the process enables the use of spinel ferrites other than franklinite, comprising cuprospinel ($CuFe_2O_4$), trevorite ($NiFe_2O_4$) or cobalt ferrite ($CoFe_2O_4$) for the debromination of the NBFRs.

13. A thermochemical method for debromination of novel-brominated flame retardants (NBFRs) using Zn-based metal oxides comprising:
   mixing the NBFRs comprising tetrabromobisphenol A 2,3-dibromopropyl ether (TD or TBBPA-DBPE) and tetrabromobisphenol A diallyl ether (TAE or TBBPA-DAE) with the Zn-based metal oxides comprising zinc oxide (ZnO) and franklinite ($ZnFe_2O_4$);
   subjecting the mixture to co-pyrolysis in a thermal reactor;
   capturing bromine radicals to form metal bromides, thereby restricting emission of brominated species from the NBFRs; and recovering bromine-free hydrocarbons.

14. The thermochemical method of claim 13, further comprising an ice trap downstream of the thermal reactor to collect condensable fractions and a sodium wash trap to collect non-condensable fractions.

15. The thermochemical method of claim 14, the ZnO captures bromine radicals into metal bromides during the thermal decomposition of the NBFRs and serves as an effective debromination agent by achieving approximately 92% capture of hydrogen bromide (HBr) gas during the co-pyrolysis.

16. The thermochemical method of claim 15, wherein thermogravimetric analysis (TGA) indicates a pyrolytic run up to 500° C. with a ramp of 10° C./min and the NBFRs treated with the ZnO produce a trivial amount of brominated compounds of approximately 0.83% relative area.

17. The thermochemical method of claim 16, wherein the NBFRs treated with the ZnO produce pyrolyzed residues (pyrochar), non-condensable gases and condensates, wherein the pyrochar retains the metal bromides comprising $ZnBr_2$, the non-condensable gases comprise inorganic gases and methane, and the condensates comprise phenol and the trivial amount of brominated compounds.

18. The thermochemical method of claim 17, wherein the bromine-free hydrocarbons comprise the phenol as a condensable product formed by the β-scission debromination reaction from the parental molecular skeleton, and the methane gas.

19. The thermochemical method of claim 18, wherein ion chromatography (IC) analysis demonstrates a low emission of less than 8% of the HBr gas during the ZnO treatment, due to the capture of the bromine radicals into the $ZnBr_2$ and further validated by FT-IR gas analysis.

20. The thermochemical method of claim 19, wherein the Zn-based metal oxides are sourced from electrical arc furnace dust (EAFD) and the metal oxides convert into their respective metal bromides during the co-pyrolysis, enabling selective extraction of zinc from the EAFD.

* * * * *